US00PP10488P

United States Patent [19]

Pieters et al.

[11] Patent Number: Plant 10,488

[45] Date of Patent: Jul. 7, 1998

[54] VRIESEA CULTIVAR 'CATHY'

[76] Inventors: Luc Pieters; Caroline DeMeyer, both of Koewegstraat 4, 9270 Laarne, Belgium; Arie Stofbergen, Leeuwenhoekweg 30; Leendert Stofbergen, Leeuwenhoekweg 32, both of 2661 CZ, Netherlands

[21] Appl. No.: 803,514

[22] Filed: Feb. 20, 1997

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Cushman Darby & Cushman IP Group of Pillsbury Madison & Sutro LLP

[57] ABSTRACT

A new and distinct variety of Vriesea plant resulting as a spontaneous somoclonal variation among propagules of 'Christiane' from tissue culture. This new plant, named 'Cathy', is characterized by having good vigor and an inflorescence of a dark reddish purple, deepening to near black as the blooming plant ages, rather than the usual brilliant red of the parent Vriesea 'Christinae'. With the exception of the coloration of the inflorescence, the newly discovered sport 'Cathy', is phenotypically similar to the parent variety 'Christiane'.

2 Drawing Sheets

BACKGROUND OF THE INVENTION

Our present invention is that of a new distinct cultivar of plant in the genus Vriesea within the family Bromeliaceae, which is the result of a sponaneous sport appearing among plantlets of Vriesea Christiane created by tissue culture techniques.

Plants of the genus Vriesea have long been desirable, decorative plants due to their long-lasting, ornamental inflorescence and symmetrical foliage. Predominating among commercially grown varieties of Vriesea have been numerous hybrids with bright red inflorescences. Among these is Vriesea Christiane, which has been in commercial production in Belgium for many years. It has been the continuing goal of plant breeders to produce compact Vriesea plants having large, brilliantly colored inflorescences combined with ease of growing. Although arguably surpassed in one characteristic or another by other Vriesea hybrid varieties, Vriesea Christiane has withstood the test of time. Due to the complex hybrid parentage of current commercial Vriesea varieties, including Vriesea Christiane, the plants can be reproduced only through vegetative reproduction, and are commonly reproduced using tissue culture techniques.

In the course of raising many thousands of plants of Vriesea Christiane to full blooming maturity, joint inventors Arie Stofbergen and Leendert Stofbergen at Bergschenhoek, Nederland, identified and isolated a single plant which differed dramatically from all others. The single plant had an inflorescence in which the floral bracts were not the usual brilliant red of Vriesea Christiane, but were dark reddish purple, deepening to near black as the blooming plant aged.

Joint inventors Luc Pieters and Caroline DeMeyer acquired the single mutant plant and successfully reproduced it vegetatively by offsets at Laarne, Belgium. The asexually reproduced progeny of the mutation have retained the characters of the mutation, and the new variety has now proved to be suitable for asexual reproduction by means of tissue culture propagation.

SUMMARY OF THE INVENTION

Our new variety can be readily distinguished from Vriesea Christiane by the purple color of its floral bracts, and can be immediately distinguished from all commercially grown Vriesea hybrids by its combination of solid purple floral bracts and multi-branched inflorescence.

Other than color of the floral bracts, our invention is substantially the same as Vriesea Christiane, but the brilliant red of the inflorescence of Vriesea Christiane is replaced by a dark purple inflorescence having reddish undertones.

Our invention differs from all known varieties of Vriesea having purple inflorescence color by having a branched inflorescence. In Belgium the only regularly grown Vriesea variety with purple coloration in the inflorescence is Vriesea "Purple Cockatoo," which produces a single, relatively short bloom spike approximately 20–30 cm. tall, with a tendency to bend slightly, rather than remaining stiffly erect. Additionally, Vriesea "Purple Cockatoo" has deep purple coloration at the tips of the floral bracts, with the coloration becoming weaker toward the base of the bracts, creating the impression of a delicae feather-shaped inflorescence edged in dark purple with a lighter center. Individual plants of Vriesea "Purple Cockatoo" may produce inflorescences with such a pale central area that the inflorescence appears to be greenish with purple edges. In comparison, our new variety is multi-branched, easily producing five to six feather-shaped paddles when given good cultural conditions, with the individual branches radiating from a stiffly erect central spike 35–40 cm. tall, creating the impression of a dark purple torch. The purple coloration is uniform, becoming darker with age, and never showing pale green coloration at the base of individual floral bracts.

Other single-spiked Vriesea varieties with purple inflorescences have been cultivated in the United States and elsewhere under the names Vriesea "Lav," V. "Purple Haze," V. "Purple Marie," V. "Mint Julep," V. "Purple Cascade" and V. "Purple Pendent." These varieties are readily distinguished from our new variety by their single-inflorescence, compared to the compound, multiple-branched inflorescence of our new variety. Additionally, the variety v. "Mint Julep" has mottled leaves, perhaps indicative of having V. hieroglycphica among its parentage, rather than having the glossy, solid green leaves of our new variety. The inflorescences of V. "Purple Cascade" and V. "Purple Pendent" are not erect, but bend downward.

Only one previous Vriesea variety is known to have had a multiple-branched, purple-colored inflorescence. V. "Ranifera" is reported to have been a cultivar of the well known Vriesea "Poelmanii" isolated over a decade ago. However, it is no longer available, at least in the commercial market. Reportedly, V. "Ranifera" suffered from erratic growth and proved unsuitable for commercial production. In comparison, our new variety is a dependable, strong grower forming a symmetrical rosette of well-shaped leaves. Because V. "Ranifera" is no longer available, it is not possible to make further direct comparison between its inflorescence and that of our new variety. Presumably, V. "Ranifera" would be distinguishable from our new variety to the same extent as V. "Poelmanii" is distinguishable from V. "Christiane." Under like cultural conditions grown in Belgium, V. "Poelmanii" is readily distinguishable from V. "Christiane" by having fewer branches in the inflorescence (3–5 compared to 5–6 for V. "Christinae"); individual floral bracts somewhat bulbous in shape rather than flat paddle-like in shape; inflorescence branches of V. Poelmanii are generally longer and larger, but commence closer to the foliage rather than having the floral spike rising above the foliage before floral branching commences; and the inflorescence branches of V. "Poelmanii" tend to be arranged closely to one another rather than being fully separated, creating the impression of a single, heavy mass of color rather than an open, airy burst of color.

BRIEF DESCRIPTION OF THE DRAWINGS

The accompanying photographs clearly depict the new variety.

DETAILED DESCRIPTION

Figure 1:
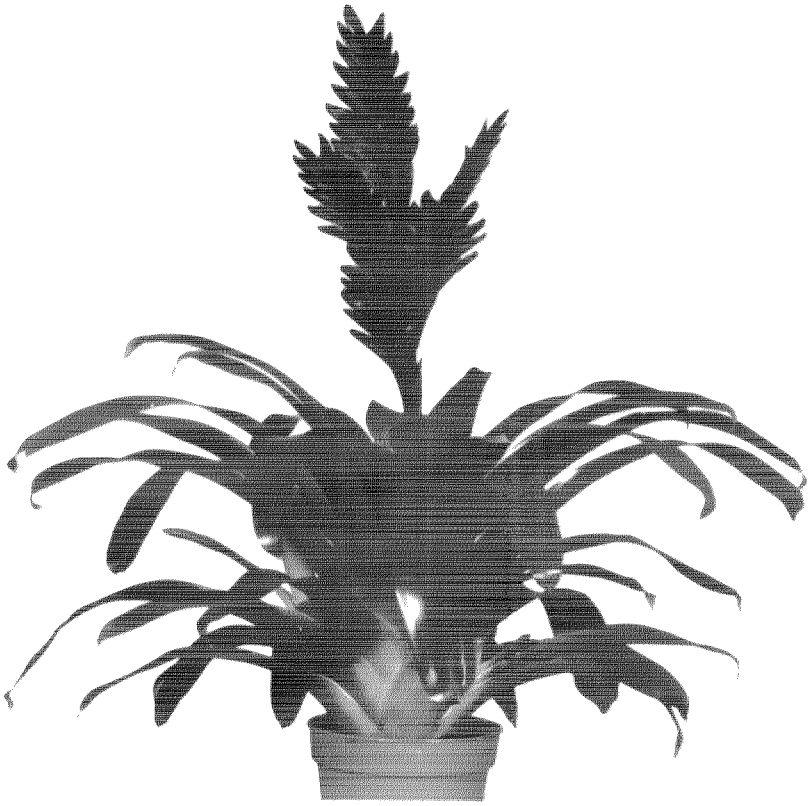
FIG. 1: shows Vriesea "Cathy" in full bloom, disclosing the conformation and overall appearance, particularly including the inflorescence branching habit and purple coloration.
Figure 2:
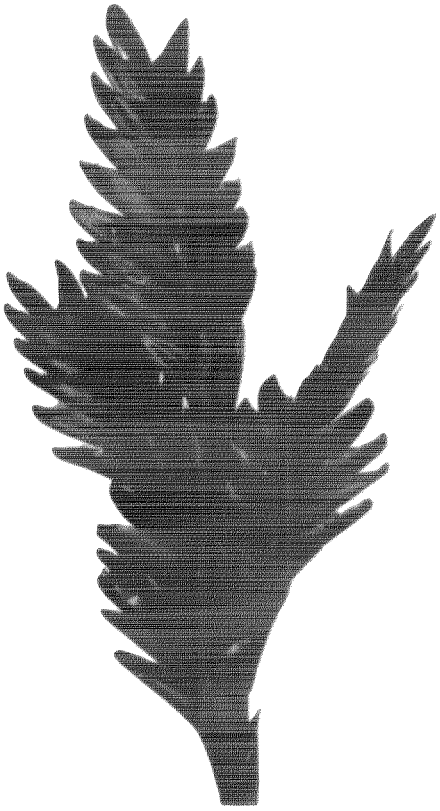
FIG. 2: shows a close-up of the inflorescence.

The following is a detailed description of our new variety, based on observations of specimens grown in Laarne, Belgium. Physical characteristics may vary in accordance with cultural conditions, such as light intensity, fertilization programs, temperature, day length, humidity and other cultural factors.

I. Parentage:

The new variety is a spontaneous mutation found as a sport among plantlets of Vriesea "Christiane."

II. Propagation:

Holds its distinguishing characteristics through succeeding generations of asexually reproduced plants.

III Form:

The plant forms a symmetrical rosette of green leaves approximately 45 cm. in diameter, or somewhat larger depending upon cultural conditions, with an erect multi-branched inflorescence purple in color.

IV. Growth:

A comparatively fast growing plant within the genus Vriesea. Under growing conditions prevailing in Belgium, which are cooler and with lower light intensity compared to conditions prevailing in Central and South Florida and Southern Calif., the current centers for commercial growing of bromeliads in the United States of America, the plant can be raised from tissue-cultured micro-cutting to a plant in full bloom in 42 months. A tissue-cultured micro-cutting will grow to transplantable plantlet size in nine months, without supplementary fertilization. An additional 17 months is required to reach standard commercially saleable size. After an additional 13 months of growth, the plant can be artifically induced to bloom by application of acetylene. Full flowering begins within three months thereafter. The vigorous growth rate of our new variety is similar to that of Vriesea "Christiane."

Resistance to disease organisms appears to be similar to that of other Vriesea hybrids and mutations. The new variety has not been found to be particularly susceptible to any disease organisms, nor particularly resistant.

V. Blooming habit:

The inflorescence rises from the center of the rosette-shaped foliage to form a torch-shaped inflorescence approximately 40 cm. tall. The inflorescence is approximately 14–16 cm across (width). Branching commences approximately 10 cm. above the foliage. The lower inflorescence branches are approximately 6–8 cm. long and 5–6 cm. wide. Ascending the flower stalk, the branches become progressively longer, reaching approximately 8–10 cm. in length, while retaining the same width. The stalk terminates in a floral bract approximately 14 cm. long.

A. Scape bracts.—Purple, approximately matching The Royal Horticultural Society Colour Card 187A. Each individual bract is approximately 3.75 cm. in length. The bracts are tightly configured, overlapping at their bases and separating at the tips from which individual flowers emerge. The stalk from which the floral bracts project is pale green, The Royal Horticultural Society Colour Card 137A and 137B.

B. Flowers.—The flowers emerge from the floral bracts located on the spikes branching from the floral stalk. Flower petals are primarily yellow, The Royal Horticultural Society Colour Card 9A, with tips bright green, Royal Horticultural Society Colour Card 143A.

VI. Foliage:

A. Size.—The lowermost leaves are approximately 27 cm. long and 6 cm. wide at the base of the leaf, with the leaf narrowing toward the outer tip to approximately 2.5 cm. in width. The upper leaves, upon reaching full length, are approximately 33 cm. long, and 4 cm. wide at the base, narrowing toward the outer tip to approximately 2 cm. in width.

B. Shaep.—Lanceolate with rounded tip, not sharp, entire, smooth.

C. Texture.—Shiny, smooth.

D. *Color.*—The upper leaf surface is bright green, The Royal Horticultural Society Colour Chart 139A, and the underside of the leaves is a somewhat lighter green, The Royal Horticultural Society Colour Card 137A and 137B.

We claim:

1. A new and distinct cultivar of Vriesea plant, named 'Cathy', substantially as herein shown and described, characterized as to novelty by the unique combination of an erect multi-branched inflorescence reddish purple in color and also being dependably vigorous in growth.

* * * * *